United States Patent [19]

Ashford

[11] 4,324,136
[45] Apr. 13, 1982

[54] BETA GAUGE MECHANISM

[75] Inventor: R. Daniel Ashford, Davenport, Iowa

[73] Assignee: Aluminum Company of America, Pittsburgh, Pa.

[21] Appl. No.: 72,621

[22] Filed: Sep. 5, 1979

[51] Int. Cl.³ .................. G01N 21/86; G01N 21/89; G01N 23/16; G01N 23/18

[52] U.S. Cl. ................................. 73/159; 250/572; 356/429

[58] Field of Search ............... 73/159; 356/444, 429, 356/430, 381; 250/571, 572, 570

[56] References Cited

U.S. PATENT DOCUMENTS

| | | | |
|---|---|---|---|
| 3,157,915 | 11/1964 | Gilbo | 356/429 |
| 3,190,261 | 6/1965 | Ziffer . | |
| 3,244,206 | 4/1966 | Bossen . | |
| 3,332,279 | 7/1967 | Tompos . | |
| 3,474,668 | 10/1969 | Mangan . | |
| 3,741,663 | 6/1973 | Nevins | 250/572 |
| 4,031,752 | 6/1977 | Sanders | 73/159 |

Primary Examiner—Gerald Goldberg
Assistant Examiner—Denis E. Corr
Attorney, Agent, or Firm—Max L. Williamson

[57] ABSTRACT

Apparatus for supporting transducer heads in a transducer measuring device that is used for measuring or monitoring characteristics of a continuously produced or processed strip material. The apparatus occupies a minimum amount of space and provides for angularly raising the upper transducer head from its measuring position in a direction which is coincident with the direction of travel of the strip material in order to minimize the danger of damage to the head and give ready access to the strip material.

1 Claim, 6 Drawing Figures

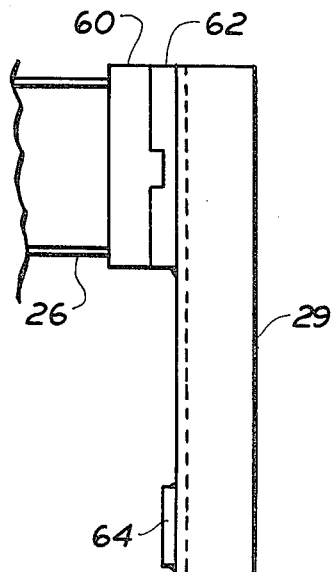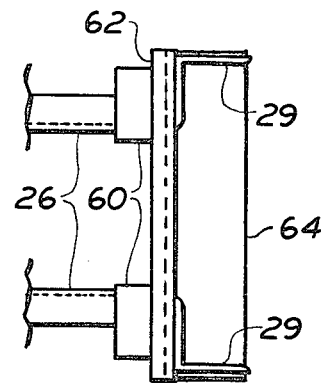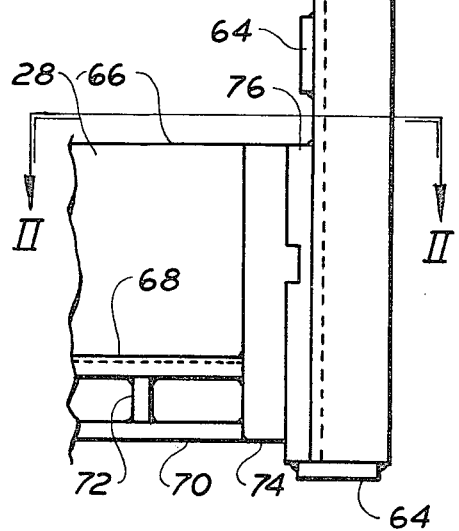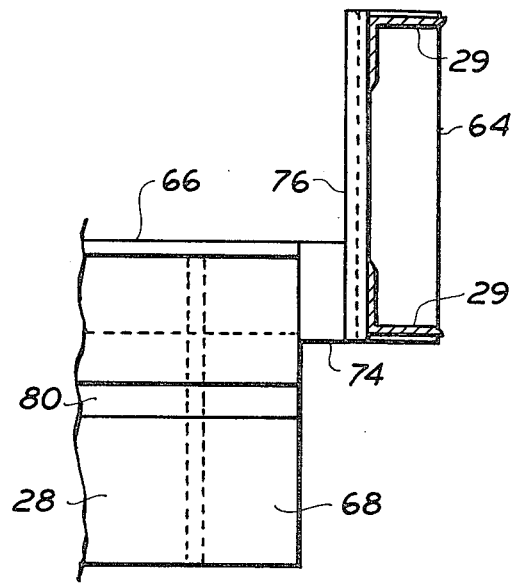
FIG. 4  FIG. 5  FIG. 6

BETA GAUGE MECHANISM

BACKGROUND OF THE INVENTION

1. Field of Art

This invention relates to devices for measuring characteristics of continuously rolled strip products and more particularly to the apparatus to support the device in the desired measuring position in relation to the strip product.

2. Brief Description of the Prior Art

Many products and materials are produced or processed in a continuous strip form at one or more stages of production. Depending upon the product or material, it is desirable to monitor or measure certain characteristics of the product as it is being manufactured or processed. For example, in the manufacture of nearly all sheet products, whether it be metal, plastic, paper or wood veneer, thickness of the product is important, and it is advantageous to continuously measure or monitor the thickness in order that changes may be made in the processing of the product, if necessary, to keep the thickness of the product within some allowable tolerance range.

Other examples of measurable characteristics that are important in product manufacture are flatness in metal sheet manufacture, moisture content in sheet paper and textiles, and thickness of applied coatings, such as paint, on coiled sheet metal.

A well-known method for taking desired measurements on continuously processed products is to use transducers which typically comprise a radiation source, a pair of heads, one a sender and the other a receiver, and an indicating instrument to display or record the measurement being taken. Typically, one head of the transducer is positioned below the sheet or strip product being processed horizontally and the other head is supported above the product opposite and coaxially aligned with the lower head. Thus, a signal from the radiation source, such as an X-ray or beta ray, is transmitted from the sending head through the material to the receiver head and the receiver head is adapted to generate an electrical signal in response thereto that is recorded or displayed on an appropriate instrument in units relating to the material characteristic being measured.

A common support device for the transducer heads is a channel-shaped structure having an upper arm and a lower arm disposed above and below the strip material being processed transverse to the flow of the strip material. The upper and lower transducer heads are mounted in coaxial alignment on the channel arms with sufficient space between the opposing heads to allow passage of the strip material. The support system may include a drive means so that the channel-shaped structure or the heads may be moved transverse to the direction of movement of the strip material being produced or processed so that measurements may be made across the width of the strip or to move the transducer heads out of the way when convenient to gain unrestricted access to the strip.

One example of a channel-shaped transducer support system is disclosed in Ziffer U.S. Pat. No. 3,190,261. A system is described which employs two transducer units to monitor and control the thickness of a coating being applied to a continuously moving strip of paper. Opposing beta gauge sending and receiving heads are affixed to the ends of a channel-shaped structure which is slidably mounted to a lower carrying member which extends transversely across the process material strip. One transducer unit measures the thickness of the paper before the coating is applied and a second unit measures the thickness of the material after coating. By synchronizing the movement of the first and second transducer units in traverse across the width of material, comparative measurements may be made to reveal the thickness of the applied coating.

Mangan U.S. Pat. No. 3,474,668 discloses a similar support means of transducer heads in a method for controlling the profile of continuously rolled strip steel material.

Other patents which disclose channel-shaped transducer head support structures which are adapted for movement in a direction transverse to the flow of material being processed are Tompos et al U.S. Pat. No. 3,332,279 and Bossen U.S. Pat. No. 3,244,206.

Although the use of channel-shaped structures as a support means for transducer heads is adequate and satisfactory for the production and processing of many strip materials, space limitations sometime make it impractical or undesirable to use such a structure.

Accordingly, a support means for transducer heads employed in a system for measuring various characteristics of a continuously produced or processed strip material is desired which can be installed in a minimum amount of space and is adapted to permit one or both of the transducer heads to be moved from their measuring position to a position that conveniently allows access to the strip material.

SUMMARY

This invention provides support apparatus for opposed sending and receiving transducer heads that are a part of a measuring system used to monitor or control a measurable characteristic of a continuously produced or processed strip material.

It is an object of this invention that the support apparatus occupy a minimal amount of space.

Another object of this invention is to provide support apparatus that permits movement of the upper transducer head in an angularly upwardly direction transverse to the width of the material or in the direction of travel of the strip material.

A further object of this invention is to provide support apparatus whereby the transducer heads mounted thereon may be fixed or movable transverse to the direction of movement of the strip material being processed.

BRIEF DESCRIPTION OF THE DRAWINGS

The above and other objects and advantages of the invention will be more fully understood and appreciated with reference to the following description and the drawings appended thereto wherein:

FIG. 4 is a partial elevation drawing of a rigid frame assembly used to anchor the heads and head support apparatus in a fixed relationship to the strip material.

FIG. 5 is a partial top view of an upper portion of the frame assembly shown in FIG. 4.

FIG. 6 is a cross-sectional view along the line II—II in FIG. 4 showing a top view of a lower support member for supporting a lower transducer head.

DESCRIPTION OF A PREFERRED EMBODIMENT OF THIS INVENTION

Although it will be apparent from the following description and explanation of the attached drawings that the apparatus of this invention may be used to support transducer heads for measuring or monitoring characteristics of other materials, for ease of description and explanation the preferred embodiment herein described is used to support transducer heads for measuring the thickness of a continuously rolled strip of aluminum alloy foil material.

Figure 1:
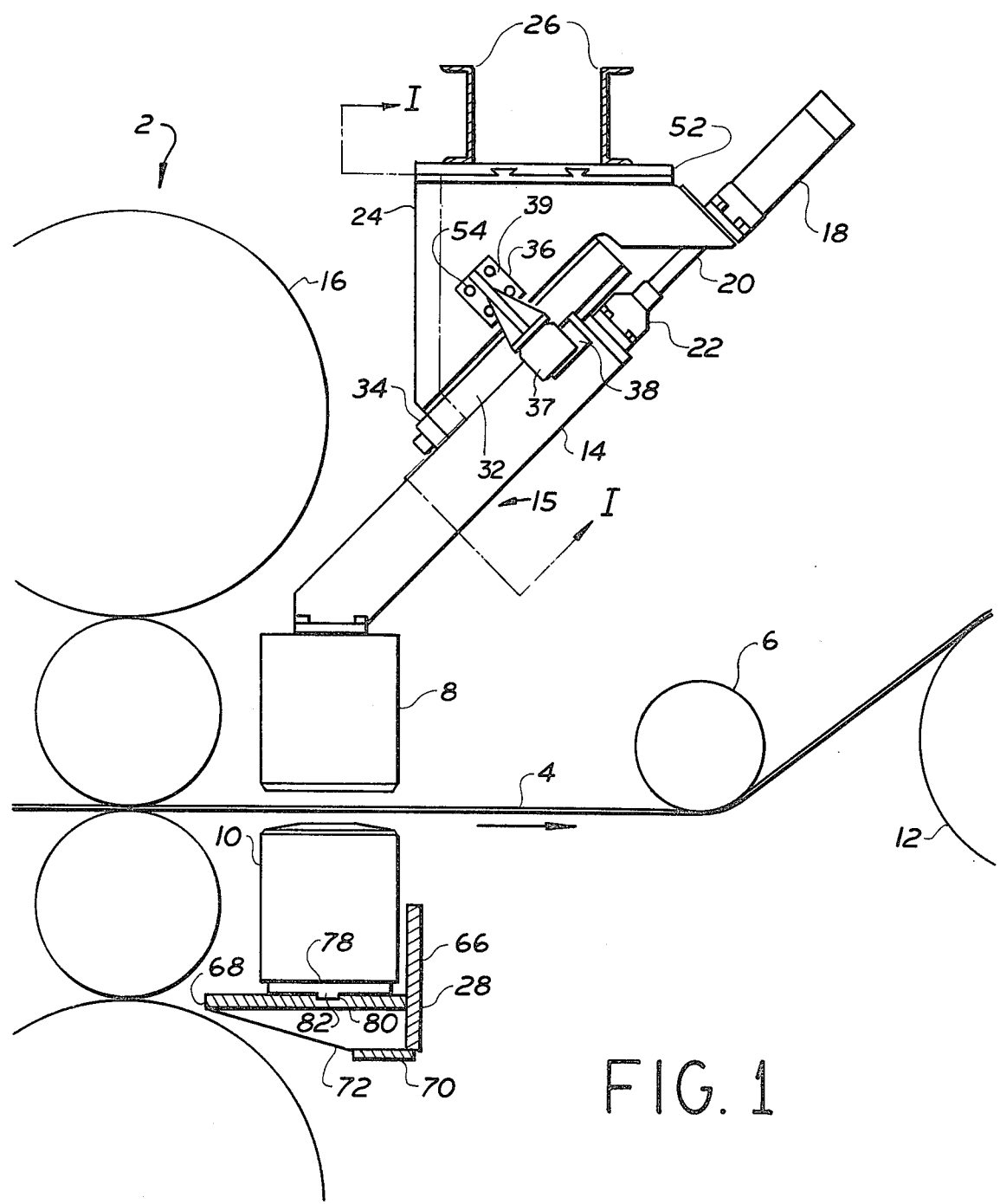
FIG. 1 is an elevation view of transducer heads supported in measuring position in relation to a continuously processed strip of material by the apparatus of this invention, and a cross section of part of the frame members used to anchor the heads and support apparatus in a fixed relationship to the strip material.

Referring to FIG. 1, a typical aluminum alloy foil mill has a roll stand 2 comprising a plurality of rolls to reduce the thickness of aluminum alloy reroll material to the desired thickness of the aluminum alloy strip foil material 4, an idler roll 6 to maintain the strip material 4 in a proper relationship to the upper and lower transducer heads 8 and 10, and a rewind arbor 12. In the production of aluminum alloy foil, aluminum alloy material is passed continuously from a reroll coil (not shown), through the roll stand 2, between the transducer heads 8 and 10 coaxially aligned in their measuring position, and subsequently wound on the rewind arbor 12. The generally horizontal plane assumed by the material 4 in traveling from roll stand 2 to idler roll 6 is called a pass line. It is not unusual that space available between the roll stand 2 and the idler roll 6 or space limitations on either side of the mill will not permit the use of a transducer measuring device when the heads are supported by channel-shaped support apparatus as disclosed in prior art.

As will now be explained, the apparatus of this invention permits positioning of transducer heads 8 and 10 in any location across the width of the strip material 4 within a limited space between the roll stand 2 and idler roll 6. The upper transducer head 8 is attached to the lower end of the upper head support member 14 so that the bottom surface of the upper transducer head 8 is parallel to the top surface of the strip material 4. The upper head support member 14 projects upwardly from the upper transducer head 8 in a direction that may be vertical or at an angle away from vertical depending upon the space available. In the preferred embodiment herein described, the distance between the outer surface of the upper roll 16 in the roll stand 2 and the idler roll 6 necessitates positioning the upper transducer head 8 in close proximity to the roll stand 2, and the upper transducer head 8 cannot be raised in a true vertical direction because of the interference of the upper roll 16.

It is desirable to be able to move the upper transducer head 8 from its measuring position as shown for at least three reasons. One is to provide access for the threading of material through the roll stand 2 to the rewind arbor 12 when starting the mill to produce material from a new rewind coil (not shown). Another reason is to minimize the danger of damage to the transducer head 8 when effecting a change in the rolls of the roll stand 2, and the third reason is to make it easier to remove "cobbles" as they occur. A "cobble" is created whenever a malfunction of the rolling process occurs such that the roll stand 2 and reroll arbor 12 are out of synchronization with one another. When the mill is operating properly, the speed of the reroll arbor 12 is synchronized with the speed of the roll stand 2 so that the strip material 4 is maintained on the desired pass line and may be continuously and uniformly wound on the arbor 12. To accomplish this purpose, a slight tension is maintained on the strip material 4 by the proper relationship in speed between the rewind arbor 12 and the roll stand 2. Should this relationship be disturbed so that the tension is too great, the strip material 4 may tear interrupting the desired flow of material and cause the strip material 4 to follow an erratic path upon its exit from the roll stand 2. Other malfunctions of the process may also occur to disrupt the proper roll and arbor speed relationship and cause the strip material 4 to be diverted from its normal flow path and produce this undesirable result. The jammed or piled-up strip material between the roll stand 2 and the rewind arbor 12 created by such a malfunction is called a "cobble", and it is obvious that in clearing the "cobble" it is desirable to be able to move the upper transducer head 8 to a position to ease the clearing or minimize the danger of damage to the head 8.

In the preferred embodiment of this invention herein described, the upward movement of the upper head 8 from its measuring position and support member 14, hereinafter called the support assembly 15, is in a direction approximately 45° measured from the vertical.

The upward movement of the support assembly 15 and subsequent downward movement to return the upper head 8 to its measuring position are controlled and accomplished by the actuation of a piston contained within a hydraulic cylinder 18 connected to the upper end of the support member 14 through the cylinder piston rod 20 and clevis 22. The upper head 8 may be moved upward from its measuring position as shown by the action of a hydraulic fluid forcing a piston connected to the piston rod 20 within the hydraulic cylinder 18 to move upward and thus raise the support assembly 15 and likewise may be moved downward to return to its measuring position from its raised position by reversing the flow of hydraulic fluid.

An upper bracket 24 is attached to upper frame members 26. The upper frame members 26 extend across the width of the rolling mill and are attached on both ends to vertical frame members 29, as shown in FIGS. 4 and 5, which extend downward and are anchored on both sides of the mill to the floor or some lower portion of the mill apparatus in a fixed relationship to the pass line of the strip material.

An upper interlock block 60 is attached by welds to each end of upper frame members 26. An upper interlock plate 62 is attached by welds to an inner upper portion of vertical angle members 29 so that the vertical angle members are in a spaced apart relationship. Attachment of the upper frame members 26 to the vertical frame members 29 is accomplished by connecting interlock blocks 60 to interlock plate 62 with mechanical fasteners. A plurality of spaced apart stiffener plates 64 are attached to vertical angle members 29 to provide strength and rigidity to the frame.

An angular shaped lower support member 28, as shown in FIGS. 1, 4 and 6, is provided which also extends across the width of the mill and is anchored on both ends to the vertical frame members 29.

The lower support member 28 is comprised of a back plate 66, a shelf plate 68, a stiffener plate 70, and a plurality of generally triangular shaped gusset plates 72. The shelf plate 68 is joined along one edge by welding to a lower portion of a side of back plate 66. A plurality of generally triangular gusset plates 72 are joined to the shelf plate 68 along their top edges by welding to portions of the bottom surface of shelf plate 68 and joined along their back edges to the back plate 66 by welding to portions of a side surface of back plate 66. The gusset plates 72 provide rigidity and support to the shelf plate 68. Stiffener plate 70 extends across the bottom of lower support member 28, and is attached by welding to portions of the bottom edge surfaces of gusset plates 72 and attached along a back edge portion to a bottom edge portion of back plate 66. A lower interlock block 74 is attached by welding to portions of both ends of lower support member 28. A lower interlock plate 76 is attached on portions of both ends by welds to portions of the inner surface of vertical angle members 29. Lower support member 28 is attached on both ends to vertical frame members 29 by joining lower interlock block 74 to lower interlock plate 76 with mechanical fasteners.

A portion of the upper surface of the lower transducer head anchor plate 78 is attached to the bottom surface of the lower transducer head 10, and the anchor plate 78 is mechanically fastened to a portion of the shelf plate 68 at any point along the length of shelf plate 68. Positioning of the transducer head 10 is dependent upon the point across the width of the strip material where a measurement is desired.

Lower portions of the vertical frame members 29 may rest on and be attached to the floor of the building in which the mill is situated or may be attached to lower portions of the mill equipment.

It is obvious that the size, particular shapes and attaching means in the rigid frame system and lower support member are matters of choice and may be altered to suit particular use requirements.

Figure 2:
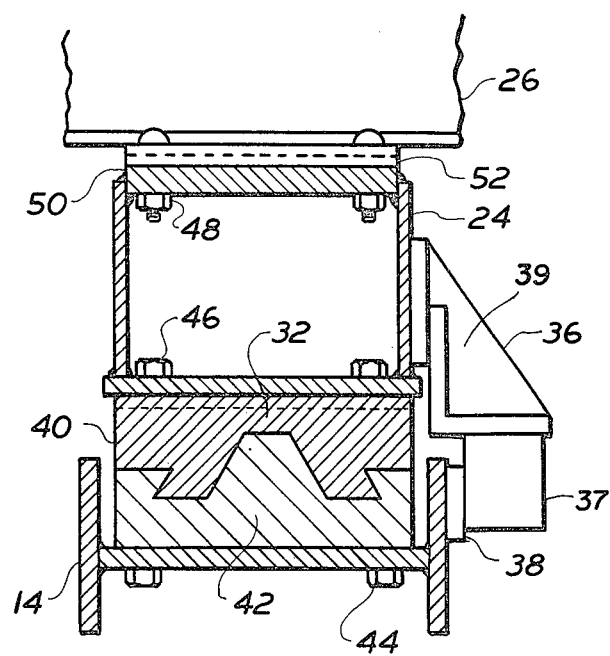
FIG. 2 is a cross-sectional view of a part of the apparatus of this invention along line I—I of FIG. 1.

Referring to FIGS. 1 and 2, the upper bracket 24 is attached to the slide assembly 32 which, in turn, is attached to the upper head support member 14. The hydraulic cylinder 18 is also attached to the upper bracket 24 so that the cylinder 18, piston rod 20, and upper head support member 14 are in coaxial alignment. The upper bracket 24 is attached to the upper frame members 26 at the desired point along the length of the frame members 26 so that the upper transducer head 8 is opposite from and coaxially aligned with the lower transducer head 10 in the measuring position.

FIG. 2 shows a cross-sectional view of a device of this invention along line I—I of FIG. 1. For ease and clarity of explanation, the cover plate 34 on the slide assembly 32 as shown in FIG. 1 is not shown. The upper head support member 14 is an I-beam shaped welded assembly of plate parts. The slide assembly 32 comprises an upper slide block 40 and lower slide block 42. The slide assembly 32 as described herein is Gilman Slide Model #DC8 as manufactured by Russel T. Gilman Inc. A dovetail fit between the upper slide block 40 and lower slide block 42 allows free longitudinal movement and prevents lateral movement of one block in relation to the other. The lower block 42 is affixed to an upper portion of the top surface of the web of the upper head support member 14 by fastener means 44. The upper block 40 is attached to a bottom surface portion of the upper bracket 24 by fastener means 46.

The upper bracket 24 is a box-shaped member rectangular in cross-section comprised of welded plates. By fastener means 48 through the top plate 50, the upper bracket 24 is attached to an anchor plate 52 that is welded to the bottom flanges of the upper frame members 26.

A deceleration valve assembly 36 is comprised of a deceleration valve 37 (shown schematically) and a bracket 39 which is attached to a side plate of the upper bracket 24 by a fastener means 54 shown in FIG. 1. A tapered plate 38 is attached to an upper end portion of the upper head support member 14 to cooperate with the deceleration valve 37, as will be explained in more detail later. The deceleration valve 37 shown is B & S AA cam operated deceleration valve series TT-160-0-CH as manufactured by the AA Division of the Brown & Sharpe Co.

Figure 3:
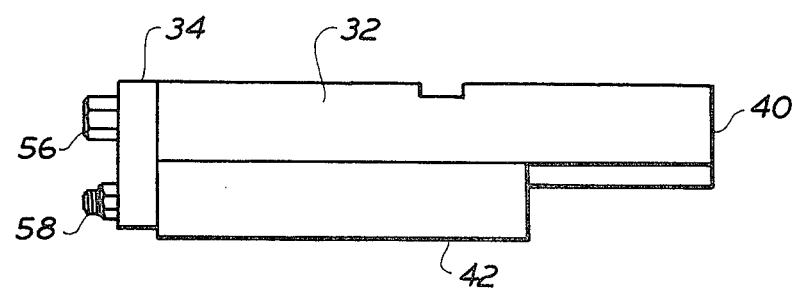
FIG. 3 is an elevation view of a slide block assembly which is one of the elements of a preferred embodiment of the apparatus of this invention.

FIG. 3 is an elevation view of the slide assembly 40 showing the cover plate 34 attached to the lower end of upper slide block 40 as the slide assembly is shown in FIG. 1. The cover plate 34 is attached to the upper slide block 40 by fastener means 56 and has set screws 58 extending through a lower portion of the block so as to permit the points of said set screws 58 to contact the end of bottom slide block 42. Tightening or loosening of the set screws permits minor adjustments to be made in the position of the upper transducer head 8 to insure its coaxial vertical alignment with the lower head 10 in the measuring position.

Referring now to FIG. 1, the apparatus of this invention is viewed with the upper and lower heads 8 and 10 in measuring position. To move the upper head 8 upward to a position that is clear of the strip material 4, a control means to the hydraulic cylinder 18 is activated causing hydraulic fluid to move a piston within the cylinder 18 upward. The upward motion of the piston translated through the connected piston rod 20 to the upper head supporting member 14 and the upper head 8 causes the head to be moved upward a maximum distance determined by the length of the stroke of the piston contained within the cylinder 18. When it is desired to return the upper head 8 to its proper measuring location, the hydraulic fluid control means is again activated so as to reverse the hydraulic pressure causing the hydraulic fluid to move the piston within the cylinder 18 downward.

The downward slide of the support assembly 15 continues until a portion of the lower end surface of the lower slide block 42 contacts the points of the set screws 58 extending through the cover plate 34. To avoid possible damage to the cover plate 34 and subsequent misalignment of the upper transducer head in the event that the lower slide block 42 might strike the set screws 58 and cover plate 34 with excessive impact, a deceleration valve 36 and actuator plate 38 are provided to reduce the downward velocity of the support assembly 15 as it approaches the measuring position.

Just prior to the lower slide block 42 striking the set screws 58, the actuator plate 38 attached to an upper portion of the support member 14 contacts a portion of the deceleration valve assembly 36 which is attached to the upper bracket 24. The plate 38 and valve 37 cooperate with each other to produce a cam action which acts as a gradual, uniform brake on the downward motion of the support assembly 15 and prevents excessive impact from the lower slide block 42 striking the cover plate 34.

The preferred embodiment of the apparatus for this invention has been described with the upper and lower heads in a fixed position relative to a direction across the width of strip material 4. It is known that a power means could be provided that would permit a synchronized movement of the upper and lower heads 8 and 10 in a direction across the width of strip material 4. For example, the lower transducer head anchor plate 78 shown in FIG. 1 could be attached to a drive means and not be mechanically fastened to lower shelf plate 68 as previously described. By providing a keyway 80 in the upper surface of shelf plate 68 and a mating keyway projection 82 in the anchor plate 78, the transducer head 10 would be slidably movable across the width of the strip material. In a like manner, the upper bracket 24 could be slidably mounted to the anchor plate 52 made to extend across the width of the mill. By known drive means, the slidable portions just described could be synchronously moved in a direction across the width of strip material 4.

It would be obvious that alternate means for components of this invention to accomplish certain functions of this invention could be employed without detracting from the spirit of the invention. For example, a pneumatic, electrical or mechanical power means might be employed to cause the upward movement of the slide assembly 15 rather than the hydraulic power means disclosed in this preferred embodiment. Likewise, a slide assembly other than the disclosed Gilman slide assembly might be used to allow the upward movement and restrict lateral movement of the support assembly 15. An alternate assembly could incorporate roller or ball bearings in one of the slide blocks and have the bearings contained within or supported by a slot or keyway in the other slide block to provide the necessary upward slidable motion.

Further, this invention is not limited to the cam action deceleration valve disclosed in this preferred embodiment. Alternate energy absorbing means are known and might feature a hydraulic or pneumatic means, spring means or friction means to brake or impede the downward motion of the support assembly 15 when returning to the measuring position.

What is claimed is:

1. Apparatus for supporting transducer heads in a measuring device used in conjunction with producing a horizontally moving continuous strip material comprising:
   (a) a rigid frame means permanently secured with respect to the horizontal strip material;
   (b) a lower horizontal support means for supporting a lower transducer head below said horizontal strip material;
   (c) a support bracket connected to said rigid frame means;
   (d) a slide assembly, having a longitudinal axis, said slide assembly comprising an upper and lower slide block adapted to slide longitudinally in relation to each other with said upper slide block rigidly attached to said support bracket and said slide assembly disposed with its longitudinal axis in a plane that is perpendicular to the horizontal strip material and parallel to the direction of travel of the horizontal strip material;
   (e) an upper support member, having a longitudinal axis, and said support member having a lower end adapted for attachment to an upper transducer head and having an upper portion connected to said lower slide block so that said support member can movably slide up and down;
   (f) a cover plate having an upper portion attached to a lower end surface of said upper slide block and a lower portion extending downward adjacent to at least a portion of a lower end surface of said lower slide block so as to provide a restraint on the downward sliding motion of said lower slide block when said upper transducer head is in a measuring position;
   (g) a hydraulic cylinder and a piston and piston rod assembly contained therein, coaxially aligned with the longitudinal axis of said support member, having the lower end of said piston rod rigidly attached to the upper end of said support member and a portion of said cylinder attached to a portion of said support bracket; and
   (h) deceleration means for gradually and uniformly braking downward motion of said lower slide block and thereby preventing said lower slide block from contacting said cover plate with excessive impact when said upper transducer head is lowered from an upper position to the measuring position.

* * * * *